(12) United States Patent
Glauser et al.

(10) Patent No.: US 8,961,901 B2
(45) Date of Patent: Feb. 24, 2015

(54) MICROFLUIDIC SYSTEM AND COATING METHOD THEREFOR

(75) Inventors: Michael Glauser, Rotkreuz (CH); Hans-Peter Wahl, Schopfheim (DE); Irio Giuseppe Calasso, Arth (CH); Emad Sarofim, Hagendorn (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 1974 days.

(21) Appl. No.: 11/828,959

(22) Filed: Jul. 26, 2007

(65) Prior Publication Data

US 2008/0056947 A1    Mar. 6, 2008

(30) Foreign Application Priority Data

Aug. 2, 2006    (EP) ..................................... 06016068

(51) Int. Cl.
*B01L 3/00*     (2006.01)
*A61B 5/15*     (2006.01)
*A61B 5/145*    (2006.01)

(52) U.S. Cl.
CPC .......... *A61B 5/1411* (2013.01); *A61B 5/14532* (2013.01); *B01L 3/502707* (2013.01); *A61B 2562/0295* (2013.01); *B01L 2300/0825* (2013.01); *B01L 2300/161* (2013.01); *B01L 2300/163* (2013.01); *B01L 2400/0406* (2013.01)
USPC ........... 422/503; 422/500; 422/501; 422/504; 436/180

(58) Field of Classification Search
CPC ................. B01L 2300/0825; B01L 2300/161; B01L 2400/0406; B01L 3/5027; B01L 9/527; B01L 2300/163; B01L 3/502707
USPC ........................................ 422/100, 500–504
See application file for complete search history.

(56) References Cited

U.S. PATENT DOCUMENTS

| | | | |
|---|---|---|---|
| 4,301,115 A | 11/1981 | Rapkin et al. | |
| 5,700,559 A | 12/1997 | Sheu et al. | |
| 6,419,842 B1 | 7/2002 | Kupka | |
| 6,673,453 B2 * | 1/2004 | Beavers et al. | 428/420 |
| 6,766,817 B2 | 7/2004 | da Silva | |
| 6,881,378 B1 | 4/2005 | Zimmer et al. | |
| 6,918,404 B2 | 7/2005 | da Silva | |

(Continued)

FOREIGN PATENT DOCUMENTS

| | | |
|---|---|---|
| EP | 0 951 930 | 6/2004 |
| EP | 1 196 243 | 6/2004 |

(Continued)

OTHER PUBLICATIONS

Fang N., Wee J.T., Leong K.W., Mao H.-Q., Chan V. "pH responsive adhesion of phospholipid vesicle on poly (acrylic acid) cushion grafted to poly(ethylene terephthalate) surface"; Colloids and Surfaces B: Biointerfaces; May 25, 2005; pp. 245-252; vol. 42; Issues 3-4; Elsevier Science BV; Amsterdam, Netherlands.

*Primary Examiner* — Dean Kwak
(74) *Attorney, Agent, or Firm* — Faegre Baker Daniels LLP

(57) ABSTRACT

A microfluidic system having a microchannel for the capillary transport of a liquid, in particular a body fluid for analytical purposes. The microchannel is provided with a surface coating comprising at least one hydrophilic substance selected from the group consisting of polyacrylic acid, polyacrylate, dextran sulfate and chondroitin sulfate. The invention also concerns a coating method that is suitable for this.

47 Claims, 3 Drawing Sheets

(56) References Cited

U.S. PATENT DOCUMENTS

| | | |
|---|---|---|
| 7,066,586 B2 | 6/2006 | da Silva |
| 2002/0120333 A1 | 8/2002 | Keogh et al. |
| 2002/0123134 A1* | 9/2002 | Huang et al. ............... 435/287.2 |
| 2002/0125135 A1* | 9/2002 | Derand et al. ................ 204/454 |
| 2002/0155481 A1* | 10/2002 | Hirota et al. ...................... 435/6 |
| 2002/0168290 A1* | 11/2002 | Yuzhakov et al. ............. 422/56 |
| 2003/0005963 A1 | 1/2003 | Schnell et al. |
| 2005/0000569 A1* | 1/2005 | Bousse et al. ................. 137/375 |
| 2005/0084681 A1* | 4/2005 | Levitt et al. .................... 428/413 |
| 2005/0130292 A1* | 6/2005 | Ahn et al. ................... 435/287.1 |
| 2005/0176678 A1 | 8/2005 | Horres et al. |
| 2005/0202504 A1* | 9/2005 | Anderson et al. ................. 435/6 |
| 2005/0214815 A1* | 9/2005 | Boschetti et al. ................. 435/6 |
| 2007/0197937 A1* | 8/2007 | Sarofim et al. ................ 600/583 |

FOREIGN PATENT DOCUMENTS

| | | |
|---|---|---|
| EP | 1 039 298 | 8/2004 |
| EP | DE 600 11 429 | 6/2005 |
| EP | 1 612 554 | 1/2006 |
| WO | WO 97/27483 | 7/1997 |
| WO | WO 01/30403 | 5/2001 |
| WO | WO 01/72220 | 10/2001 |
| WO | WO 02/089865 | 11/2002 |

* cited by examiner

MICROFLUIDIC SYSTEM AND COATING METHOD THEREFOR

RELATED APPLICATIONS

This application is related to and claims priority to European Application Serial No. 06016068.6, filed Aug. 2, 2006, the disclosure of which is expressly incorporated by reference herein.

FIELD OF THE INVENTION

The invention concerns a microfluidic system having a microchannel for the capillary transport of a liquid and a method for applying a hydrophilic surface coating to such a microfluidic system.

BACKGROUND OF THE INVENTION

Microfluidic systems are used especially in analytical systems for body fluids for example in blood sugar measuring instruments which diabetics can use themselves to monitor their blood sugar level. The system comprises a lancing member which is connected to the microchannel for the capillary transport of a body fluid. The fluid is transported by the microchannel to a collecting area in order to detect the respective measured quantity, for example the blood sugar content, separately from the lancing site. Such systems are disclosed for example in WO2006/021361 and EP 1671585, both of which are hereby incorporated by reference in their entirety, to the contents of which explicit reference is made especially with regard to the manufacture of such microstructures.

The microchannel and optionally the lancing member are manufactured from a biocompatible material i.e. a material that is inert especially towards the body fluid, which has to be capable of being mechanically stressed as well as easy to clean and sterilize. Surgical steel, such as 316L steel, for example, is particularly suitable for this but is not sufficiently hydrophilic to allow a capillary transport of aqueous body fluids through the microchannel. For this reason durable and stable hydrophilic surface coatings are sought which are also biocompatible. In addition the surface coating must allow the microchannel to fill within a very short time, preferably less than two seconds so that the body fluid can be collected rapidly. This is especially important for collecting blood for determining the blood sugar content because coagulation reactions would not yet be expected within such a short period such that the user very rapidly obtains a measuring result. Moreover, the surface coating must be compatible with at least one sterilization method, such as sterilization by means of electron rays ($\beta$-radiation), for example.

Finally an adequate long-term stability of the surface coating is desirable. This poses a problem because hydrophilic coatings usually have high-energy surfaces. This is generally thermodynamically unfavorable because the surface attempts to reduce its high energy by reducing the hydrophilicity.

SUMMARY OF THE INVENTION

The present invention generally relates to a microfluidic system including a microchannel provided with a surface coating comprising at least one hydrophilic substance selected from the group consisting of polyacrylic acid, polyacrylate, dextran sulfate and chondroitin sulfate. Generally, the surface coating is biocompatible, permanently hydrophilic and it can be sterilized after it has been applied to the surface to be coated. Thus, the surface coating may result in rapid filling times of the microchannel and resists against contamination.

Simple linear as well as completely or partially cross-linked polyacrylic acids or polyacrylates are suitable as coating materials. Polyacrylic acid and polyacrylates i.e. the neutralized derivatives of polyacrylic acid, have been previously known in the pharmaceutical industry as gelling agents for the formulation of ointments where active substances are embedded in a hydrogel matrix. Polyacrylic acids are additionally used as superabsorbers. In embodiments of the invention, surfaces manufactured from biocompatible material such as high grade steel or other inert metals can be coated with polyacrylic acids and/or with salts thereof. The polyacrylic acid or the salt thereof can be applied directly from a dispersion onto the surface to be coated. The liquid may be removed to form a transparent layer. Generally, the method according to embodiments of the invention allows a coating of mass products such as disposable microfluidic systems.

In embodiments, the surface can be hydrophilized by an immersion coating using dextran sulfate or chondroitin sulfate. A single layer may be formed in this process which adheres by means of an ionic bond. The two sugar sulfates are substances which are biologically inactive and are thus also acceptable for in vivo applications, wherein a body fluid is collected by lancing.

According to embodiments of the microfluidic system according to the invention, the hydrophilic surface coating has a contact angle for distilled water of less than 80° and may be less than 40°.

A lancing member may be connected to the microchannel, said lancing member being provided with the surface coating. It is feasible to provide the entire surface of the microchannel and/or the lancing member with the surface coating. The surface of the microchannel or of the lancing member to be coated may comprise a biocompatible material, such as high-grade steel. The microchannel can be formed on a flat support as a semi-open groove-shaped capillary channel. The microchannel may be connected to a test field in order to detect an analyte in the fluid.

Other embodiments of the invention comprise an analytical system for body fluids and in particular a portable blood sugar measuring device having a microfluidic system in the form of consumables that can be stored in a magazine.

In such embodiments, a hydrophilic surface coating comprises at least one substance selected from a group comprising polyacrylic acid, polyacrylate, dextran sulfate and chondroitin sulfate in a liquid, in particular water, and brought into contact with a surface to be coated. The liquid is removed whereby the previously amorphous substance forms a hydrophilic layer.

In an embodiment of the method according to the invention the surface to be coated can be cleaned before applying the surface coating. Suitable methods are oxygen low-pressure plasma methods, corona discharge methods and acid etching methods or any other suitable method understood by a person skilled in the art.

An embodiment of the invention provides that polyacrylic acid is dispersed in a liquid, in particular water, and the dispersion obtained is applied to the surface to be coated. The dispersion may be neutralized with a base. This allows the dispersion to be adjusted to the pH of the fluids to be examined, for example of blood, so that the dispersion is particularly compatible with the fluid to be examined.

The dispersion can be diluted before application, for example, with the dispersing liquid such as water. In this manner it is possible to adapt the viscosity of the dispersion to the respective method that is used to apply it to the surface to be coated. Suitable methods are for example pipetting, spraying, dip-coating methods or spin-coating methods. After the dispersion has been applied, the dispersing fluid is removed by a drying process for example heating to thus form the desired surface coating.

According to another variant of the coating method, the surface to be coated is immersed in an aqueous solution containing dextran sulfate and/or chondroitin sulfate wherein the layer obtained in this manner is bound firmly to the surface in particular by an ionic bond. In order to remove excess substances, it is advantageous when the surface is washed preferably in a water bath after the hydrophilic layer has been applied.

BRIEF DESCRIPTION OF THE DRAWINGS

The above-mentioned and other features of this invention and the manner of obtaining them will become more apparent and the invention itself will be better understood by reference to the following description of an embodiment of the present invention taken in conjunction with the accompanying drawings, wherein.

Corresponding reference characters indicate corresponding parts throughout the several views. The exemplification set out herein illustrates one embodiment of the invention, in one form, and such exemplification is not to be construed as limiting the scope of the invention in any manner.

DETAILED DESCRIPTION OF AN EMBODIMENT OF THE INVENTION

Figure 1:
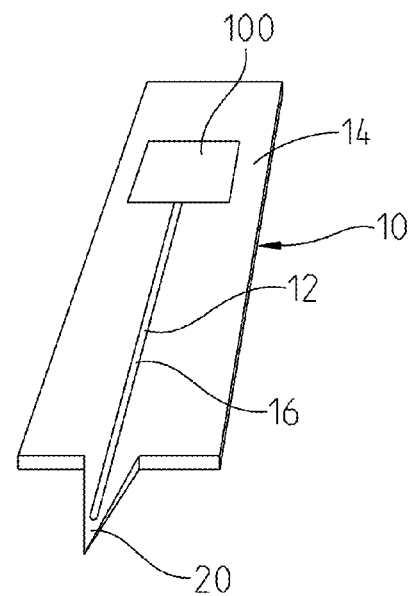
FIG. 1 shows a microfluidic system in the form of a microsampler in a diagrammatic representation.

For the purposes of promoting an understanding of the principles of the invention, reference will now be made to the embodiments illustrated in the drawings, which are described below. It will nevertheless be understood that no limitation of the scope of the invention is thereby intended. The invention includes any alterations and further modifications in the illustrated devices and described methods and further applications of the principles of the invention, which would normally occur to one skilled in the art to which the invention relates.

Figure 2:
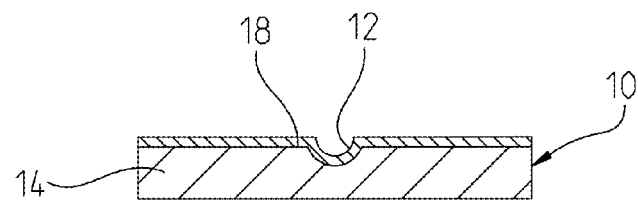
FIG. 2 shows an enlarged (not to scale) cross-section of the microsampler of FIG. 1.

The microfluidic system 10 shown in FIGS. 1 and 2 as a so-called microsampler forms a disposable element for receiving and providing body fluid, especially blood or tissue fluid, for analytical purposes and in particular for blood sugar measurements. For this purpose a microchannel or capillary channel 12 is provided which alone, without external actuation, allows liquid to be transported by capillary action from a distal receiving site to a proximal target site. The channel 12 is incorporated in a groove shape into a flat support 14 made of high-grade steel sheet for example by mask etching or laser cutting. The surface 16 of the channel 12 formed by the upper side of the support 14 is provided with a hydrophilic surface coating 18 which assists in filling the channel 12.

The distal end of the channel 12 is located in the area of a lancing member 20 which can for example be inserted into a finger while the proximal end of the channel is brought into fluidic connection with a test field 100 which contains a suitable test chemistry for the glucose detection. For this purpose the microsampler 10 can be inserted into a hand-held device that can also be operated by laymen like those that are already known for the analysis of test strips. Apart from biocompatibility and sterilizability, generally the hydrophilic coating 18 should be sufficiently durable for repeated use.

EXAMPLE 1

Figure 3:
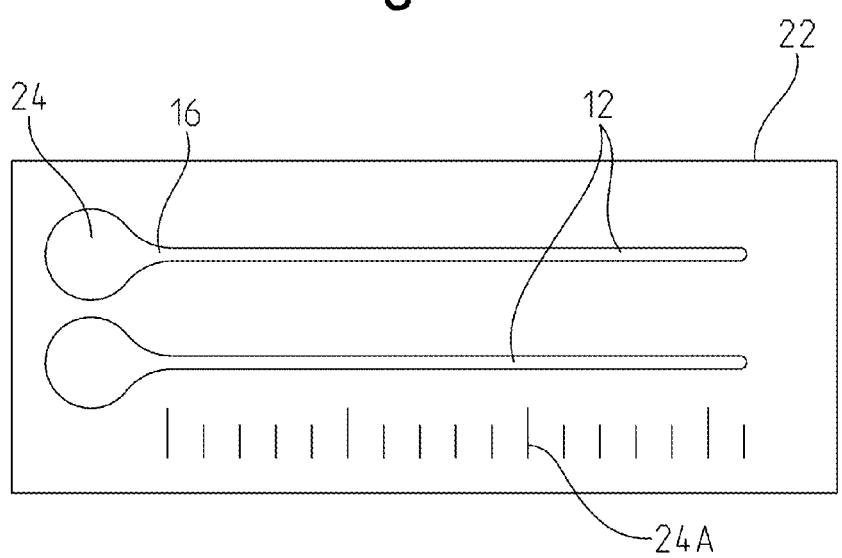
FIG. 3 shows a test plate as a microfluidic system in a top-view.

For a long-term stability study, test plates 22 made of surgical steel were provided according to FIG. 3 with two semi-open microchannels 12 about 0.63 inch (16 mm) long and about 0.0079 inch (0.2 mm) wide. An application site 24 for blood was made as an extended depression at the beginning of each of the channels 12. The entire surface of the test plates 22 was coated in the manner described below. In this manner the recessed surface 16 of the microchannels 12 and the application site 24 were also provided with a hydrophilic surface coating 18. A line scale 24A was introduced on a longitudinal side of the steel plates 22.

In one embodiment of the invention, the coating is based on the basic principle of using commercially available polymerized polyacrylic acids (PAA) (i.e. those that are already traditionally used as gelling agents in the pharmaceutical industry and as superabsorbers in the required purity) as starting materials for the production of a hydrophilic surface coating.

A polyacrylic acid which in the present example is the product of the Sigma-Aldrich Company No. 43, 532-5 "Poly (acrylic acid), potassium salt, lightly cross-linked" is dispersed in a suitable liquid for the respective application case which in the present example is water. Instead of a cross-linked polyacrylic acid, it is also possible to use a non-cross-linked, linear polyacrylic acid. A viscous dispersion or gel matrix is obtained by the dispersing.

This gel matrix can then be neutralized with a base in order to adjust the pH to a desired pH. If for example a microfluidic system for transporting a body fluid is to be coated, the dispersion or gel matrix can be adjusted to the pH of the fluid to be examined which in the present example is blood. A wide variety of bases are suitable for this, in particular sodium hydroxide solution, potassium hydroxide solution or basic amino acids. A polyacrylic acid salt or polyacrylate is formed in this process. The choice of a suitable base depends on the respective requirements for the biocompatibility and toxicology of the surface coating to be produced. In the example the pH was adjusted with KOH to about 7.0.

There is a large increase in the viscosity of the dispersion during the neutralization because the individual strands of the polyacrylic acid unfold due to electrostatic repulsion. Even after neutralization the dispersion can be adjusted by dilution to the desired viscosity which is best suited to the respective selected application method. In the example, the neutralized dispersion is diluted with water to such an extent that a very low-viscosity dispersion was obtained. In addition the long-polyacrylic acid threads were mechanically reduced in size.

The surface 16 to be coated and activated was cleaned for coating with an oxygen low-pressure plasma method. Subsequently the test plate 22 was immersed in the very low-viscosity dispersion. After superficial drying, water was removed from the dispersion by heating to about 176° F. (80° C.) A dried polyacrylate layer remained which adhered firmly to the test plate 22. The layer was transparent and not discernible with the naked eye so that presumably a very thin film of polyacrylate had formed. This transparent layer is strongly hydrophilic and is thus water-attracting.

The test plates 22 were heat sterilized after the coating for about 3 hours at about 226° F. (130° C.) and then packaged in glass which is a very pure packaging material.

The test plates 22 treated and packaged in this manner were stored for about 3 months at about 95° F. (35° C.). These storage conditions represent a model for storage for about 2 years at room temperature. Test plates 22 were removed at regular intervals and tested for filling length as well as for filling time of the microchannels 12.

Figure 4:
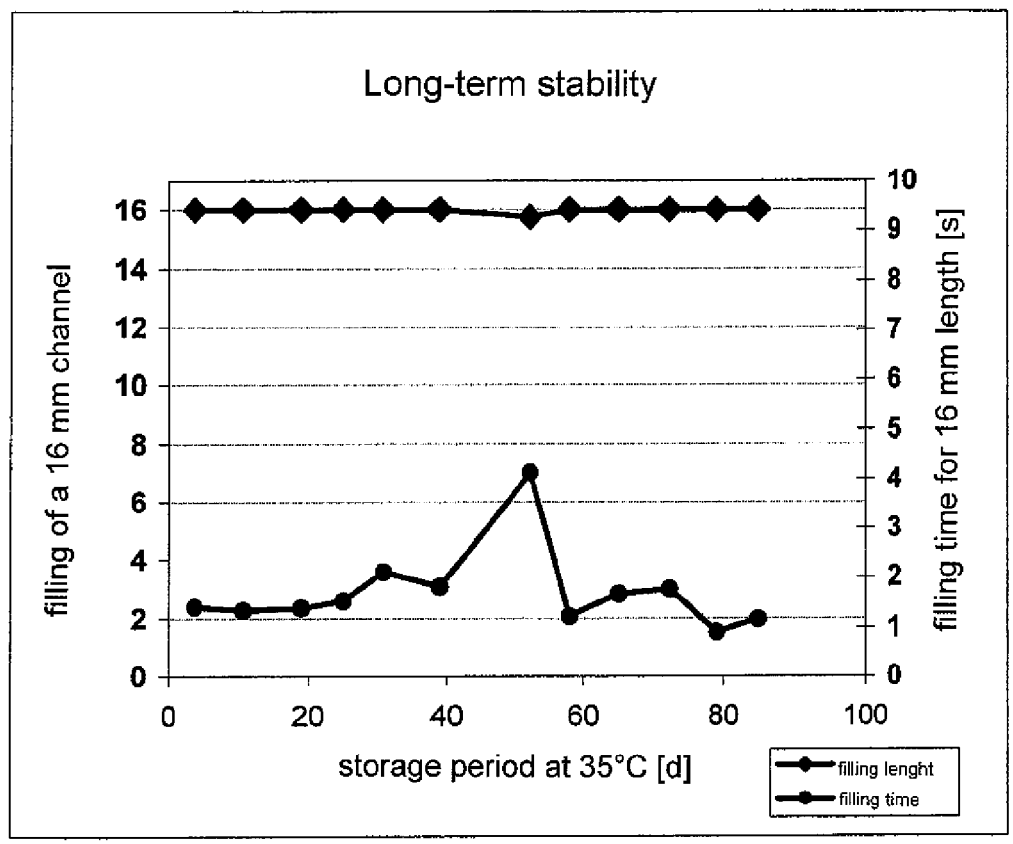
FIG. 4 shows a measuring diagram of a stability study using the test plate according to FIG. 3.

According to FIG. 4 it turned out that the microchannels 12 were completely filled by all samples. The average filling time was about two seconds and even a slight improvement was observed after a long storage period. Expressed as a contact angle, the path of about 0.63 inch (16 mm) to be filled corresponds to a contact angle of less than 10°. Hence the coating proved to be very stable and its hydrophilicity did not diminish during the storage period.

It was also checked whether the described coating can be sterilized with electron beams (β rays). For this purpose plates made of surgical steel were provided with an about 0.63 inch (16 mm) long microchannel and coated as described above. Subsequently half of the plates were packaged in PET bags and sterilized with β radiation (10 MeV, 25 kGy). Afterwards the respective average filling length and the respective average filling duration of the irradiated and of the non-irradiated plates was determined and compared. The result is shown in table 1.

TABLE 1

| | Ø filling length | Ø filling duration | standard deviation of the filling period |
|---|---|---|---|
| sterilized | 0.63 inch (16.0 mm) | 1.65 sec. | 0.26 sec. |
| not sterilized | 0.63 inch (16.0 mm) | 1.82 sec. | 0.56 sec. |

These results show that the sterilization with β rays has no adverse effect on the coating.

In addition a biocompatibility test according to ISO 10993 (test for in vitro cytotoxy, ISO 10993-5, test for irritation ISO 10993-10, test for delayed-type hypersensitivity ISO 10993-10) was carried out after the β sterilization. For this purpose the product from Sigma-Aldrich No. 43,532-5 "poly(acrylic acid), potassium salt, lightly cross-linked" was used. For the biocompatibility test this product was adjusted with KOH to a pH of about 7.0. In addition the long polyacrylic acid strands were mechanically reduced in length. This product was dispersed in water and applied to a surface of surgical steel as described. This coating passed all three tests which are well-known and were carried out according to regulations and can thus be used for the desired application in conjunction with microfluidic systems.

EXAMPLE 2

In another embodiment a polyacrylate is used which does not have to be homogenized and as a pharmaceutical base material has a high controlled purity. The product is Carbopol 971P NF Polymer from the Noveon Company which is referred to as C971 in the following.

During the preparation of the coating a 0.01% dispersion was not used directly because this results in a negligible change in the pH. It should be noted that the buffer effect of water in combination with small amount of weak acid is unfavorable for a titration. For this reason a 0.1% dispersion was prepared as follows:

About 0.73 gallon (300 ml) milli-Q water was placed first in a large beaker glass. The water was stirred with the aid of a bar mixer such that a suitable vortex was visible. Then about 0.011 ounce (300 mg) C971 was weighed onto weighing paper and then added to the beaker glass. After about 20 min stirring all large agglomerates had disappeared and a viscous liquid was formed having a pH of about 3.5. Subsequently 18% (w/v) KOH was added until a pH of about 7 was reached whereby the PAA strands began to wind on at this time. Afterwards it was diluted ten-fold with milli-Q water. The 0.01% about 0.0134 oz./gal (0.1 mg/ml) dispersion obtained in this manner was used directly without filtration for the coating. Desirable results were obtained for the filling length and filling time of capillaries on test plates even after months of storage.

EXAMPLE 3

This example is based on a coating with dextran sulfate or chondroitin sulfate by means of an immersion method. The coated surfaces can then be freed of non-bound dextran sulfate or chondroitin sulfate by simply washing with sterile, distilled water. After subsequent drying the microsamplers coated in this manner are ready for further processing. The two sugar sulfates are substances which are not biologically active.

Figure 5:
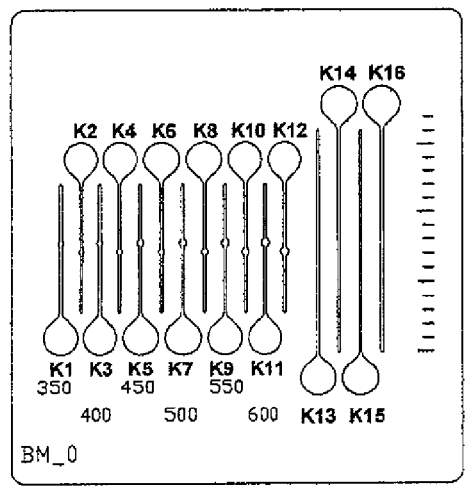
FIG. 5 shows another test plate in a top-view.

For test measurements test plates 30 made of steel having a thickness of about 0.012 inch (0.3 mm) were provided according to FIG. 5 with about 0.0079 inch (200 μm) wide capillaries K1-K16 where the capillaries had a length of about 0.354 inch (9 mm) (K1-K12) and about 0.63 inch (16 mm) (K13-K16) respectively. The middle parts of the capillaries K1-K12 have a different widening with a cuvette width of about 0.014 to 0.024 inch (350 to 600 μm).

A 1% (w/v) dextran sulfate or chondroitin sulfate solution was used as the coating agent (dextran sulfate: product number 31395 from Sigma-Aldrich; chondroitin sulfate: product number 27042 from Sigma-Aldrich; solvent: milli-Q water).

The test plates 30 were coated according to the following process steps:

1. Plasma activation: about 1 min vacuum, about 1 min vacuum and $O_2$ rinsing, about 2 min plasma.
2. Coating: about 10 min in a container containing dextran sulfate or chondroitin sulfate.
3. Washing: The coated plates were removed from the solutions, allowed to drip and then washed for about 5 min in a water bath on a shaker. Excess adsorbed dextran sulfate and chondroitin sulfate was removed by washing and a single layer of dextran sulfate or chondroitin sulfate remained.
4. Drying: The coated microsamplers were dried for about 10 min in an oven at about 176° F. (80° C.) (alternatively: blow dry in a stream of $N_2$ gas).
5. Packaging: The coated plates were shrink-wrapped in a Mylar bag.
6. Sterilization: The plates produced in this manner were sterilized by means of an electron beam.

An increased hydrophilicity of the test plates 30 was demonstrated by contact angle measurements. Untreated plates have a contact angle for distilled water of about 80°, whereas the plates coated with dextran sulfate and also with chondroitin sulfate have a contact angle of about 30°.

Figure 6:
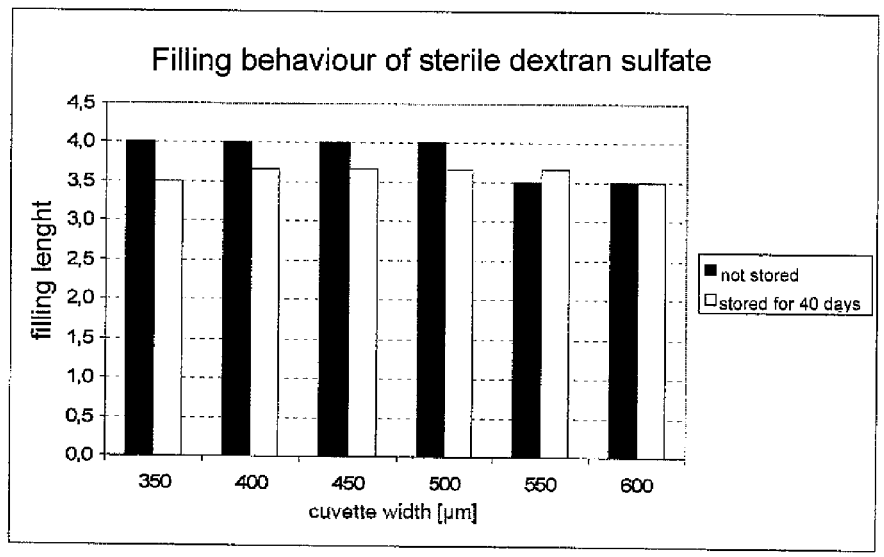
FIGS. 6 and 7 show measuring diagrams of a stability study using test plates according to FIG. 5.
Figure 7:
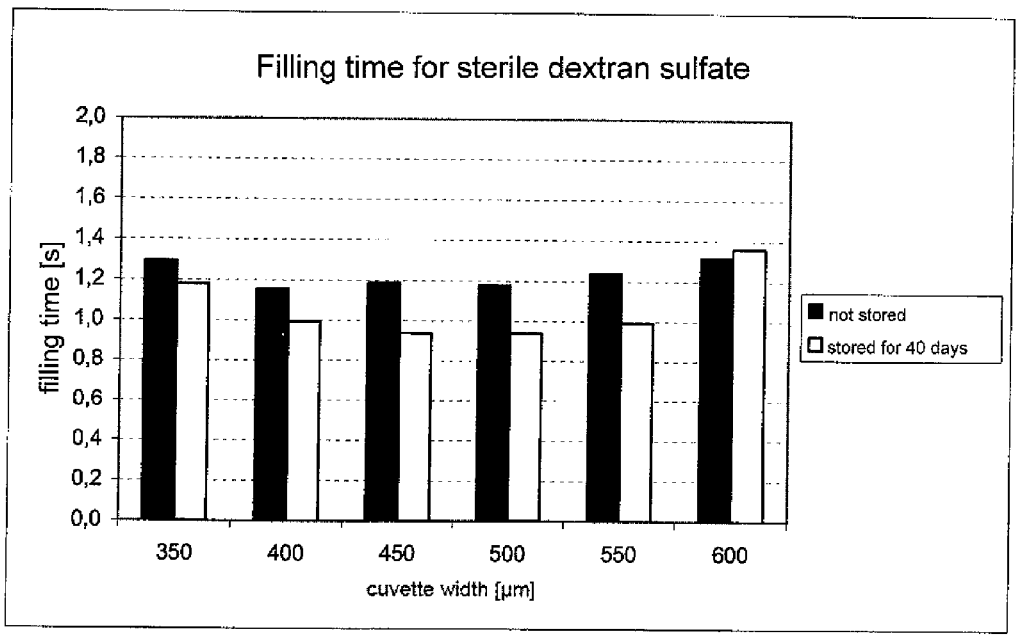

In order to assess the stability, the filling length of the capillaries K1-K12 was determined according to FIG. 6 also after approximately a 40 day storage where an ordinate value of 4 corresponds to a filling of the upper capillary section beyond the widened area. Thus the hydrophilization withstands an electron beam sterilization (25 kGy, 10 MeV) and remains stable for months. The corresponding filling times to a certain point in the semi-capillary were determined according to FIG. 7 which resulted in very good values in a range of about 1 second even after storage.

While the invention has been taught with specific reference to these embodiments, one skilled in the art will recognize that changes can be made in form and detail without departing from the spirit and scope of the invention. The described embodiments are to be considered, therefore, in all respects only as illustrative and not restrictive. As such, the scope of the invention is indicated by the following claims rather than by the description.

The invention claimed is:

1. A microfluidic system comprising:
    a microchannel for the capillary transport of a liquid; and
    a coating covering at least a portion of the microchannel comprising at least one substance selected from the group consisting of polyacrylic acid, a salt of polyacrylic acid, dextran sulfate and chondroitin sulfate.
2. The microfluidic system according to claim 1 wherein the coating further comprises a partially cross-linked polyacrylic acid.
3. The microfluidic system according to claim 1 wherein the coating has a contact angle for distilled water of less than about 80°.
4. The microfluidic system accordingly to claim 3 wherein the coating has a contact angle for distilled water of less than about 40°.
5. The microfluidic system according to claim 1 further including a lancing member connected to the microchannel.
6. The microfluidic system according to claim 5 wherein the lancing member is coated with the coating.
7. The microfluidic system according to claim 6 wherein substantially the entire surface of each of the microchannel and the lancing member is covered by the coating.
8. The microfluidic system according to claim 5 wherein the lancing member is made of a biocompatible material.
9. The microfluidic system according to claim 8 wherein the biocompatible material is a steel.
10. The microfluidic system according to claim 1 wherein the microchannel is made of a biocompatible material.
11. The microfluidic system according to claim 1 wherein the microchannel is a semi-open groove shaped capillary channel formed in a flat support.
12. The microfluidic system according to claim 1 wherein the microchannel forms a transport path from a receiving site to a collecting site for the body fluid.
13. The microfluidic system according to claim 1 wherein the microchannel, when in a connected state with a test field capable of detecting an analyte in the fluid, the microchannel abuts the test field.
14. The microfluidic system according to claim 13 wherein the analyte is blood glucose.
15. The microfluidic system according to claim 1, wherein the liquid is a bodily fluid.
16. A method of coating a microfluidic system including a microchannel for the capillary transport of a liquid comprising the steps of:
    selecting at least one substance from the group consisting of polyacrylic acid, a salt of polyacrylic acid, dextran sulfate and chondroitin sulfate in a liquid;
    dispersing the substance over at least a portion of the surface of the microchannel; and
    removing the liquid to form a hydrophilic layer.
17. The method according to claim 16 wherein the liquid is water.
18. The method according to claim 16 wherein the polyacrylic acid includes a cross-linked polyacrylic acid.
19. The method according to claim 16 further including the step of neutralizing the dispersed substance with a base.
20. The method according to claim 16 further including the step of diluting the substance prior to dispersing the substance.
21. The method according to claim 16 wherein the substrate is dispersed by a process selected from a group consisting of pipetting, spraying, dip-coating and spin-coating.
22. The method according to claim 16 wherein the liquid is removed by heating the substance following the dispersion step.
23. The method according to claim 16 further including the step of immersing the surface to be coated in an aqueous solution comprising dextran sulfate.
24. The method according to claim 16 further including the step of immersing the surface to be coated in an aqueous solution comprising chondroitin sulfate.
25. The method according to claim 16 wherein an ionic bond bonds the substance to the surface.
26. The method according to claim 16 further including the step of washing the surface in a water bath following the dispersing step.
27. The method according to claim 16 wherein the liquid is removed by drying the microchannel.
28. The method according to claim 16 wherein the liquid is removed by placing a portion of the microchannel in a stream of gas.
29. The method according to claim 16 wherein at least a portion of the microchannel is made from a biocompatible material.
30. The method according to claim 29 wherein the biocompatible material is a steel.
31. The method according to claim 16 further including the step of cleaning the microchannel.
32. The method according to claim 31 wherein the microchannel is cleaned by a process selected from the group consisting of using oxygen low-pressure plasma, using corona discharge and acid etching.
33. The method according to claim 16 further including the step of sterilizing the microchannel with an electron beam treatment.
34. A system for the capillary transport of a liquid comprising:
    a body including a surface and a microchannel formed in the surface; and
    a coating covering at least a portion of the microchannel comprising at least one substance selected from the group consisting of polyacrylic acid, a salt of polyacrylic acids, dextran sulfate and chondroitin sulfate.
35. The system as set forth in claim 34 wherein the coating is formed substantially from a partially cross-linked polyacrylic acid.
36. The system as set forth in claim 34 wherein the body includes a lancing member.
37. The system as set forth in claim 36 wherein at least a portion of the microchannel extends into the lancing member.
38. The system as set forth in claim 36 wherein the body further includes a test field abutting the microchannel.
39. The system as set forth in claim 38 wherein the test field includes at least one element capable of detecting glucose.
40. The system as set forth in claim 39 wherein the lancing member is located near a first end of the body and the test field is located near a second end of the body.
41. The system as set forth in claim 36 wherein the coating covers at least a portion of the lancing member.

42. The system as set forth in claim 41 wherein at least a portion of the body is formed from a biocompatible material.

43. The system as set forth in claim 42 wherein the lancing member is formed at least in part from a biocompatible material.

44. The system as set forth in claim 43 wherein the biocompatible material is a steel.

45. The system as set forth claim 43 wherein at least a portion of the microchannel is formed from a biocompatible material.

46. The system as set forth in claim 34 wherein the microchannel is a groove formed in the surface.

47. The system as set forth in claim 34 wherein the cross-section of the microchannel is semi-circular in shape.

* * * * *

UNITED STATES PATENT AND TRADEMARK OFFICE
CERTIFICATE OF CORRECTION

PATENT NO.        : 8,961,901 B2                                        Page 1 of 1
APPLICATION NO.   : 11/828959
DATED             : February 24, 2015
INVENTOR(S)       : Glauser et al.

It is certified that error appears in the above-identified patent and that said Letters Patent is hereby corrected as shown below:

In the Claims

Claim 45, Column 9, Line 8, delete "as set forth claim 43" insert --as set forth in claim 43--

Signed and Sealed this
Ninth Day of June, 2015

Michelle K. Lee
*Director of the United States Patent and Trademark Office*